US012766017B2

(12) United States Patent
Cao et al.

(10) Patent No.: US 12,766,017 B2
(45) Date of Patent: Oct. 20, 2026

(54) MEDICAL DEVICE COMPRISING A BALLOON-STENT ASSEMBLY AND METHODS OF USING THE SAME

(71) Applicant: SHANGHAI GOLDEN LEAF MED TEC CO., LTD., Shanghai (CN)

(72) Inventors: Hongguang Cao, Shanghai (CN); Haidong Chen, Shanghai (CN); Meijun Shen, Shanghai (CN)

(73) Assignee: BRATTEA MEDTECH CO., LTD., Shanghai (CN)

( * ) Notice: Subject to any disclaimer, the term of this patent is extended or adjusted under 35 U.S.C. 154(b) by 624 days.

(21) Appl. No.: 18/309,750

(22) Filed: Apr. 28, 2023

(65) Prior Publication Data

US 2023/0285174 A1 Sep. 14, 2023

Related U.S. Application Data

(63) Continuation-in-part of application No. 15/894,920, filed on Feb. 12, 2018, now abandoned.

(30) Foreign Application Priority Data

Feb. 13, 2017 (CN) ......................... 201710077036.3

(51) Int. Cl.

| | |
|---|---|
| ***A61F 2/958*** | (2013.01) |
| ***A61B 18/00*** | (2006.01) |
| ***A61B 18/14*** | (2006.01) |
| ***A61F 2/90*** | (2013.01) |
| ***A61F 2/954*** | (2013.01) |

(52) U.S. Cl.

CPC ................ *A61F 2/958* (2013.01); *A61F 2/90* (2013.01); *A61B 2018/00214* (2013.01);

(Continued)

(58) Field of Classification Search

CPC ............ A61B 18/1492; A61B 17/2202; A61B 17/320068; A61B 17/320725; A61B 18/1815; A61B 2018/00285; A61B 2090/065; A61B 2017/22061; A61B 2018/1422; A61B 2017/320069; A61B 2018/00577; A61B 2018/0022; A61B 2018/00601; A61B 2018/1412; A61B 2018/00821; A61B 2018/0044; A61B 2018/1861; A61B 17/320069; A61B 2017/22051; A61B 2017/22065; A61B 2018/00214; A61B 2018/1415;

(Continued)

(56) References Cited

U.S. PATENT DOCUMENTS 5,133,732 A * 7/1992 Wiktor ...................... A61F 2/88 623/1.22
6,245,076 B1 * 6/2001 Yan ........................... A61F 2/95 606/108

(Continued)

*Primary Examiner* — Bradford C. Blaise
(74) *Attorney, Agent, or Firm* — George Guosheng Wang; Upstream Research and Patent LLC

(57) ABSTRACT

The present invention provides a medical device with a balloon-stent assembly comprising a stent, a balloon within the stent, and an ablation member. The medical device can be useful for a combined procedure of balloon angioplasty, radiofrequency ablation, and stent placement. The invention exhibits numerous merits such as simpler and precise operation, and a single device for multiple applications.

19 Claims, 17 Drawing Sheets

(52) U.S. Cl.
CPC ................. *A61B 2018/0022* (2013.01); *A61B 2018/1412* (2013.01); *A61B 2018/1415* (2013.01); *A61F 2/954* (2013.01)

(58) Field of Classification Search
CPC .... A61F 2/90; A61F 2/958; A61F 2/95; A61F 2002/9505; A61F 2002/9511; A61F 2002/9583; A61M 25/104
USPC ............................................................ 606/41
See application file for complete search history.

(56) References Cited

U.S. PATENT DOCUMENTS

2002/0045930 A1* 4/2002 Burg ......................... A61F 2/95 606/108
2002/0188341 A1* 12/2002 Elliott ..................... A61F 2/958 623/1.1
2003/0018362 A1* 1/2003 Fellows ............ A61B 18/1492 607/5
2006/0047336 A1* 3/2006 Gale ....................... A61F 2/958 623/1.11
2007/0073375 A1* 3/2007 Gundale ................... A61F 2/91 623/1.11
2008/0039928 A1* 2/2008 Peacock .................... A61F 2/95 623/1.15
2011/0263960 A1* 10/2011 Mitchell ................. A61F 2/958 623/1.15
2013/0296853 A1* 11/2013 Sugimoto .......... A61B 18/1492 606/49
2015/0164401 A1* 6/2015 Toth ..................... A61B 5/0538 606/41
2017/0035496 A1* 2/2017 Nagale ............... A61N 1/36007
2017/0258587 A1* 9/2017 Gloss .................... A61F 2/2418

* cited by examiner

MEDICAL DEVICE COMPRISING A BALLOON-STENT ASSEMBLY AND METHODS OF USING THE SAME

CROSS-REFERENCE TO RELATED APPLICATIONS

This non-provisional application is a Continuation-in-Part of U.S. patent application Ser. No. 15/894,920 (abandoned), filed on Feb. 12, 2018, which expressly claims the benefit of priority under the Paris Convention based on Chinese Application No. 201710077036.3, filed on Feb. 13, 2017. The entire disclosures of the two prior applications are incorporated herein by reference.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

FIELD OF THE INVENTION

The present invention generally relates to a medical device comprising a balloon or a balloon-stent assembly and methods of using the same. Although the invention will be illustrated, explained and exemplified by embodiments in vascular and interventional radiology (VIR), it should be appreciated that the present invention can also be applied to other minimally invasive image-guided diagnosis and treatment of disease.

BACKGROUND OF THE INVENTION

Stenosis and stricture are an abnormal narrowing in a blood vessel or other tubular organ. For stenosis, the narrowing is caused by lesion that reduces the space of lumen (e.g. atherosclerosis). For stricture, the narrowing is caused by contraction of smooth muscle, e.g. achalasia, and prinzmetal angina. One way to solve the problem is angioplasty, also known as balloon angioplasty and percutaneous transluminal angioplasty (PTA). Balloon angioplasty is a minimally invasive, endovascular procedure to widen narrowed or obstructed arteries or veins, typically to treat arterial atherosclerosis. A deflated balloon attached to a catheter is passed over a guide-wire into the narrowed vessel and then inflated to a fixed size. The balloon forces expansion of the blood vessel and the surrounding muscular wall, allowing an improved blood flow. A stent may be inserted at the time of ballooning to ensure the vessel remains open, and the balloon is then deflated and withdrawn.

Take coronary angioplasty as an example. The therapeutic procedure can treat the stenotic (narrowed) coronary arteries of the heart found in coronary heart disease. These stenotic segments may be caused by the buildup of cholesterol-laden plaques from atherosclerosis. In a percutaneous coronary intervention (PCI), the blood stream is accessed through the femoral or radial artery, and then the procedure uses coronary catheterization to visualize the blood vessels on X-ray imaging. After this, an interventional cardiologist can perform a coronary angioplasty, using a balloon catheter as described above. Metallic scaffolds such as coronary stents may then be deployed within the coronary artery segment to maintain wide luminal patency. Coronary stents are designed as permanent endoluminal prostheses that can seal dissections, create a predictably large initial segment, and prevent early recoil and late vascular remodeling. Drug-eluting stents (DESs) elute medication to reduce restenosis (the recurrence of abnormal narrowing of a blood vessel) within the stents. Coronary stents are used in most interventional procedures. Stent-assisted coronary intervention has replaced coronary artery bypass graft (CABG) as the most common revascularization procedure in patients with coronary artery disease (CAD) and is used in patients with multi-vessel disease and complex coronary anatomy.

As mentioned above, restenosis is the recurrence of stenosis after a procedure. The main cause of restenosis following angioplasty procedures is due to vessel wall trauma created during the procedure. Evidence has shown that scar tissue forms as endothelial cells that line the inner wall of the blood vessel re-generate in response to the vessel wall injury created during angioplasty.

In radiofrequency ablation (RFA), part of the electrical conduction system of the heart, tumor or other dysfunctional tissue is ablated using the heat generated from medium frequency alternating current (in the range of 350-500 kHz). When the RF energy is delivered via catheter, it is called radiofrequency catheter ablation. One advantage of radio frequency current over low frequency AC and DC pulses is that it does not directly stimulate nerves or heart muscle and therefore can often be used without the need for general anesthetic. Another advantage is that it is very specific for treating the desired tissue without significant collateral damage.

Advantageously, the present invention provides a medical device comprising a balloon or a balloon-stent assembly and methods of using the device, which exhibit numerous improvements over three traditional areas combined: balloon angioplasty, radiofrequency ablation, and stent placement.

SUMMARY OF THE INVENTION

One aspect of the present invention provides a medical device having a balloon-stent assembly. The assembly includes a stent, a balloon within the stent, and an ablation member.

Another aspect of the invention provides a medical device comprising a balloon, an electrode, and a pedestal. The pedestal is located between (and contacts both) the electrode and an external surface of the balloon to increase a height of the electrode above said external surface, i.e. height along the normal direction of said external surface.

Still another aspect of the invention provides a medical process comprising providing a medical device comprising a balloon and an electrode; maneuvering the balloon and the electrode near a tissue; inflating or deflating the balloon so that the electrode contacts or presses the tissue with a controllable contacting pressure; and ablating the tissue only when the contacting pressure falls within a predetermined range. In many embodiments, inflating the balloon and ablating the tissue are carried out simultaneously.

A further aspect of the invention provides a medical device with a balloon-stent assembly comprising a balloon expandable stent, a balloon within the balloon expandable stent, and a breakable tether that links the balloon expandable stent and the balloon. The breakable tether is so configured that, while the balloon expandable stent is being expanded by the balloon and after the balloon expandable stent has been expanded by the balloon and has been placed a position in a tissue lumen or a channel within a tubular tissue structure, the breakable tether does not break apart; but while the balloon is being moved away from the already-placed balloon expandable stent or after the balloon is moved away from the already-placed balloon expandable stent, the breakable tether breaks apart without disrupting the position of the already-placed balloon expandable stent. In exemplary embodiments, the breakable tether does not wrap around the stent. The breakable tether does not wrap around the balloon either. The breakable tether does not go between any two wires of the stent. The breakable tether is not a restraining tether that restrains an expansion of the stent. The breakable tether is entirely placed within a space between the balloon expandable stent and the balloon before it breaks apart; and it does not wrap around the balloon before or after it breaks apart.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

It is also to be understood that the terminology used herein is for the purpose of describing particular embodiments only, and is not intended to limit the scope of the invention. For example, when an element is referred to as being "on", "connected to", or "coupled to" another element, it can be directly on, connected or coupled to the other element or intervening elements may be present. In contrast, when an element is referred to as being "directly on", "directly connected to", or "directly coupled to" another element, there are no intervening elements present.

Figure 1:
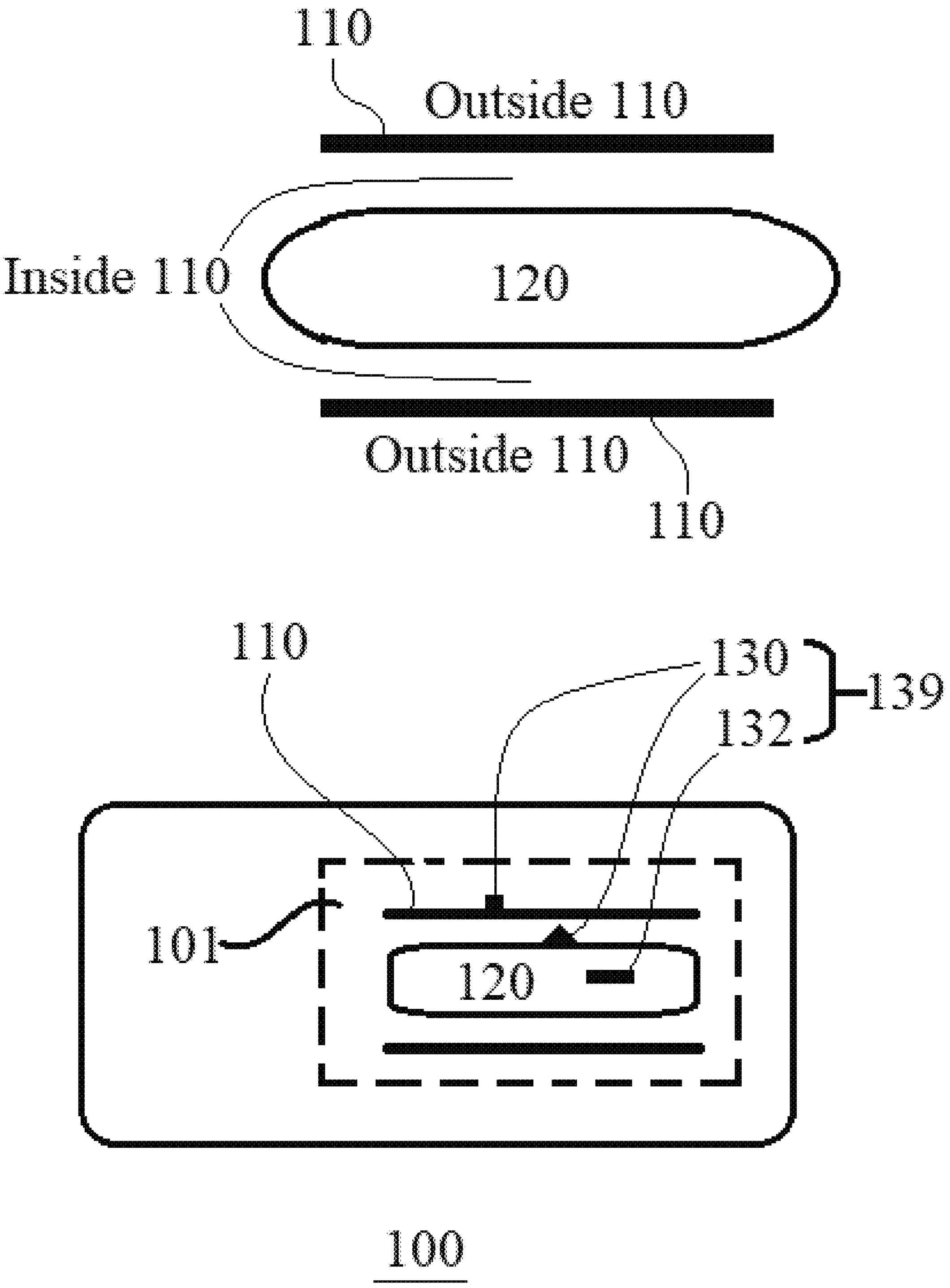
FIG. 1 schematically shows a medical device that includes a balloon-stent assembly in accordance with an exemplary embodiment of the present invention.

With reference to FIG. 1, a medical device 100 (e.g. a catheter) includes a balloon-stent assembly 101. Assembly 101 includes a stent 110, a balloon 120 within the stent 110, and an ablation member 139. Stent 110 may be any suitable metal or plastic tube to be inserted into the lumen of an anatomic vessel or duct and to keep the passageway open. Typically, stent 110 has a stent longitudinal axis and a suitable diameter, and a length along the stent longitudinal axis. Made of metals such as stainless steel alloys, platinum iridium alloys, and cobalt chrome alloy, metallic stents 110 may be a scaffold for providing a structure with sufficient radial strength (crush resistance) to address recoil and hold the vessel open over time. Stents 110 may be made of wire(s), coils, braids, a sheet, and/or tubular bodies. Balloon expandable stents in assembly 101 may be made of patterned non-degradable metallic tubes, wires, or sheet with limited inward recoil, high strength (crush resistance or crush force), and limited axial shortening upon expansion. Examples of stent 110 include expandable coronary, vascular and biliary stents, and simple plastic stents. In preferred embodiments, stent 110 is a coronary stent for coronary angioplasty, such as a bare-metal stent, a drug-eluting stent, a bio-absorbable stent, a dual-therapy stent (combination of both drug and bioengineered stent), or a covered stent. However, it should be appreciated that stent 110 may be used in other applications such as peripheral artery angioplasty (carotid, iliac, and femoral arteries). Because of the external compression and mechanical forces, flexible stent materials such as nitinol are used in a majority of peripheral stent placements. Stent 110 may also be an esophageal stent for palliative treatment of advanced esophageal cancer, and other stents for different purposes.

In balloon angioplasty, the balloon 120 merely by itself can be involved in three events: plaque fracture, compression of the plaque, and stretching of the vessel wall. These lead to expansion of the external elastic lumina and axial plaque redistribution along the length of the vessel. The balloon 120 may have suitable diameter and length sized to fit within the lumen of a vessel. As will be shown in FIGS. 17 and 18, various shapes of balloon 120 include, but not limited to, a cylindrical shape, a spherical shape, an oval shape, a conical shape, a stepped shape, a tapered shape and a dog bone shape. The balloon ends can have shapes including, but not limited to, a conical sharp corner end, a conical radius corner end, an offset neck end, a spherical end and a square end. The balloon 120 may be made from material such as a polyamide, polyethylene terephthalate (PET), polyurethane, composites, engineered nylons and equivalent materials.

The ablation member 139 may be an electrode 130 (e.g. in vivo RF electrode) on an external surface of the balloon 120, an ultrasonic wave generator 132 inside the balloon 120, and/or an electrode 130 on an external surface of the stent 110. In preferred embodiments of the invention, electrode 130 is a radiofrequency ablation (RFA) electrode. RFA is a known local treatment using a catheter to destroy tissue with heat generated by medium frequency alternating currents.

When electrode 130 is placed on an external surface of the balloon 120, it may be optionally comprised of a conductive material which is flexible and generally conforms to an outer surface of the balloon 120 during expansion of the balloon. Another electrode (in vitro RF electrode, not shown) is placed on the patient's skin to form a current loop with in vivo RF electrode 130. Alternatively or additionally, another in vivo RF electrode (not shown) is placed on an external surface of the balloon 120 to form a current loop with in vivo RF electrode 130. The electrodes are positioned so that electrical current flows between the electrodes and through the target area.

The electrodes 130 may be made of suitable electrically conductive material including but not limited stainless steel, gold, silver and other metals including shape-memory materials such as nitinol. Nitinol is an alloy with super-elastic characteristics which enables it to return to a pre-determined expanded shape upon release from a constrained position.

In an example, medical device 100 may be a cutting wire balloon catheter, to "score" a stenotic lesion in a controlled and precise manner. Scoring a lesion can lead to less procedural vessel trauma, endothelial cell re-growth and re-stenosis.

Alternatively or additionally, an ultrasonic wave generator 132 may be used as the ablation member 139. Microwave ablation (MWA) can destroy tissue with heat generated by microwaves. MWA uses electromagnetic waves in the microwave energy spectrum (300 MHz to 300 GHz) to produce tissue-heating effects. MWA can be performed using a single MW antenna or a cluster of three to achieve a greater ablation volume. Examples of MWA systems use either a 915 MHz generator or a 2450 MHz generator. The MW antennas used are straight applicators with active tips ranging in lengths from 0.6 to 4.0 cm. The antennas may be internally cooled with either room-temperature fluid or carbon dioxide to reduce conductive heating and to prevent possible thermal damage. MWA is generally used for the treatment and/or palliation of tissues such as solid tumors in patients. The oscillation of polar molecules produces frictional heating, ultimately generating tissue necrosis within solid tumors. Tumor temperatures during ablation can be measured with a separate thermal couple. Tumors may be treated to over 60° C. to achieve coagulation necrosis.

Figure 2:
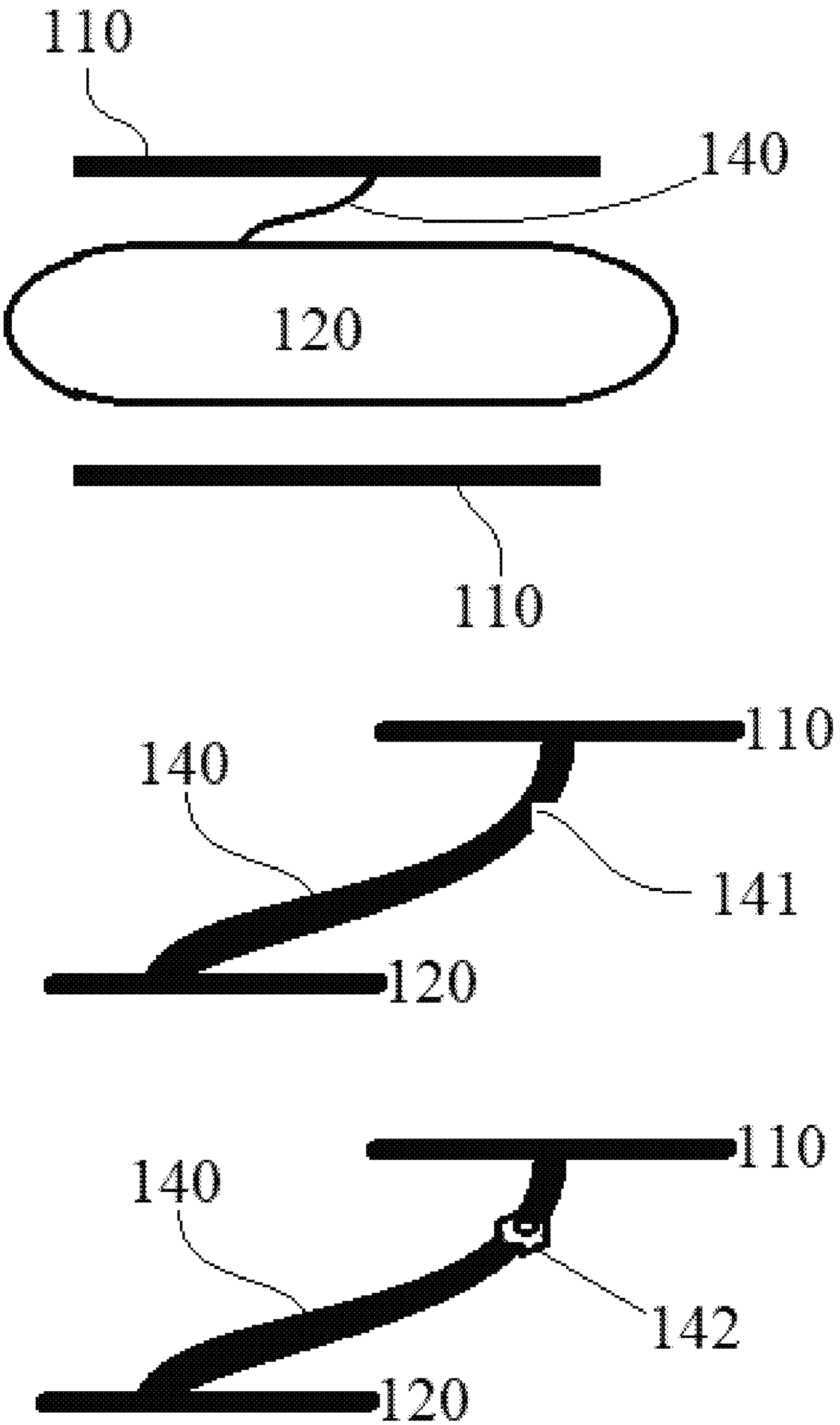
FIG. 2 is illustrates a breakable tether that links the stent and the balloon in accordance with an exemplary embodiment of the present invention.

With reference to FIG. 2, assembly 101 may include a breakable tether 140 that links the stent 110 and the balloon 120. During or after the stent 110 is properly placed, the doctor can pull/push the balloon 120 with the breakable tether 140 with a proper force, so as to break tether 140 apart without disrupting the position of already-placed stent 110. To facilitate the "breaking", breakable tether 140 may include a breakable point such as a weakened point 141 or a snap fastener 142 that is easier to break than any other points along tether 140. The length from point 141 or snap fastener 142 to stent 110 along tether 140 may be less than 30%, 20%, 10% or 5% of the total length of tether 140.

Figure 3:
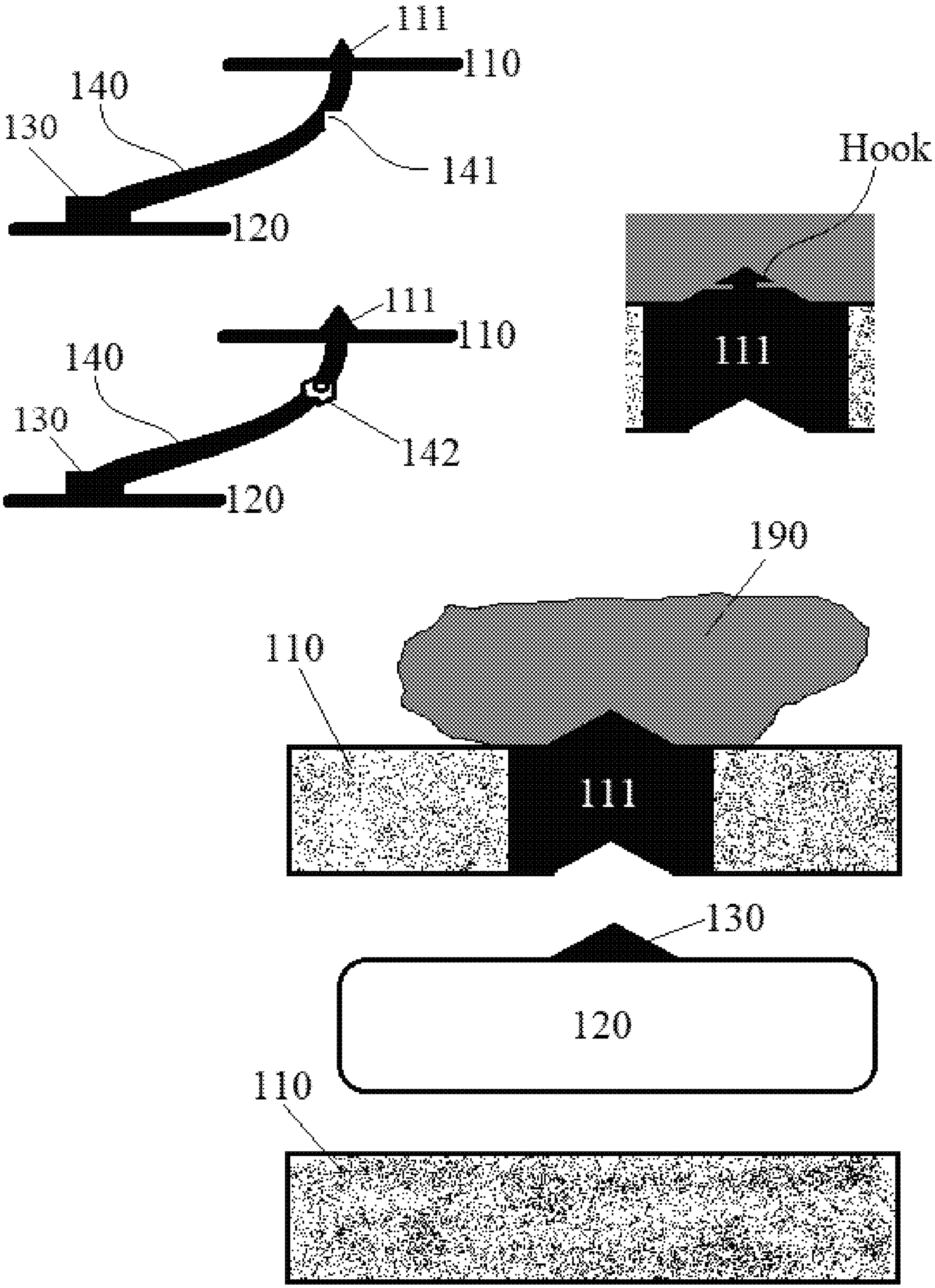
FIG. 3 illustrates an electrode extender in the stent that functions as an ablation member in accordance with an exemplary embodiment of the present invention.

With reference to FIG. 3, the stent 110 may include an electrode extender 111 that functions as the ablation member 139. Electrode 130 contacts the electrode extender 111 from inside the stent 110. Electrode 130 electrically communicates to a tissue 190 outside the stent 110 through the electrode extender 111. In an embodiment, the electrode extender 111 has an outward blade for cutting into or nailing into, and therefore anchoring to, the tissue 190. The blade may have a hook to reinforce its anchoring to the tissue 190. To facilitate a proper contact or engagement between electrode 130 and the electrode extender 111, electrode 130 may be designed as a pyramid or a cone in which the smaller end is pointing to extender 111. The base of extender 111 may have a cavity (like a negative pyramid or cone) for receiving the pyramid-shaped or cone-shaped electrode 130. As a result, electrode 130 will easily slide into the cavity during the procedure and mate or engage to extender 111 with a defined spatial interrelationship.

In an embodiment, tether 140 is used to link electrode 130 on the balloon and extender 111, and to establish electrical communication between them.

As illustrated in FIGS. 1-3, the present invention provides a medical device 100 with a balloon-stent assembly 101 comprising a balloon expandable stent 110, a balloon 120 within the balloon expandable stent 110, and a breakable tether 140 that links the balloon expandable stent 110 and the balloon 120. The breakable tether 140 is so configured that, while the balloon expandable stent 110 is being expanded by the balloon 120 and after the balloon expandable stent 110 has been expanded by the balloon 120 and has been placed a position in a tissue lumen or a channel within a tubular tissue structure, the breakable tether 140 does not break apart; but while the balloon 120 is being moved away from the already-placed balloon expandable stent 110 or after the balloon 120 is moved away from the already-placed balloon expandable stent 110, the breakable tether 140 breaks apart without disrupting the position of the already-placed balloon expandable stent 110. In exemplary embodiments, the breakable tether 140 does not wrap around the stent 110. The breakable tether 140 does not wrap around the balloon 120. The breakable tether 140 does not go between any two wires of the stent 110. The breakable tether 140 is not a restraining tether that restrains an expansion of the stent 110. The breakable tether 140 is entirely placed within a space between the balloon expandable stent 110 and the balloon 120 before it breaks apart; and it does not wrap around the balloon 120 before or after it breaks apart.

Figure 4:
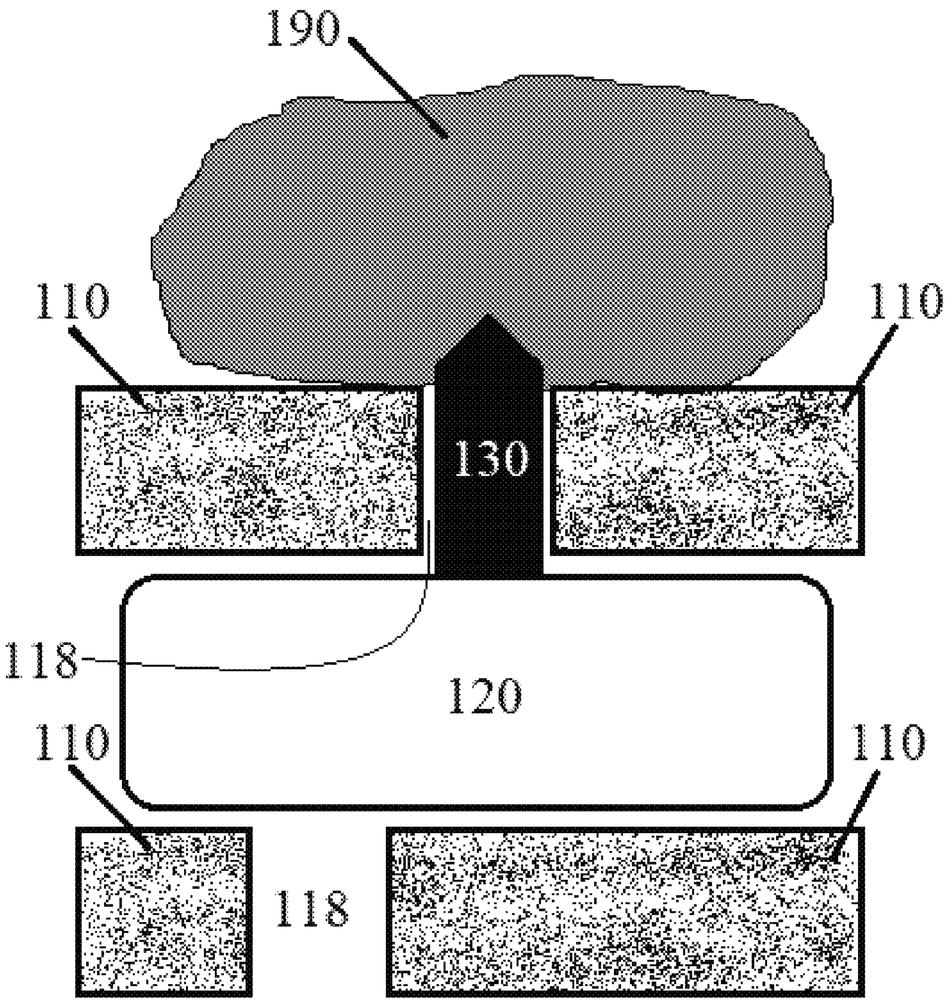
FIG. 4 demonstrates a configuration of the stent-balloon assembly in accordance with an exemplary embodiment of the present invention.

With reference to FIG. 4, the stent 110 includes a radial opening 118, which may be like a “mesh hole” of stent that is made of wires, coils, and braids. Electrode 130 can extend beyond the stent 110, or protrudes out from the stent 110, through the radial opening 118 to contact a tissue 190 outside the stent 110.

Figure 5:
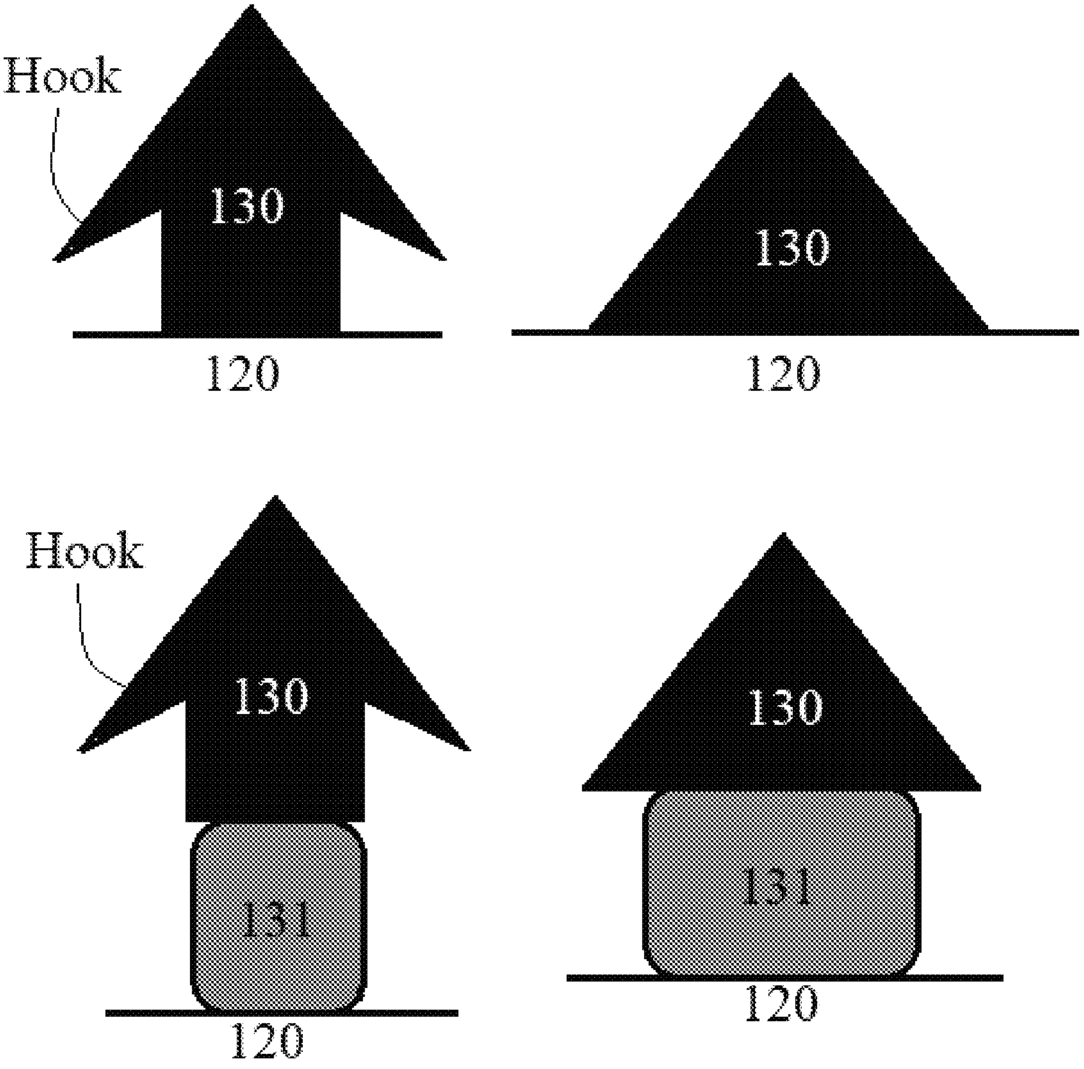
FIG. 5 depicts an ablation electrode with a pedestal beneath in accordance with an exemplary embodiment of the present invention.

With reference to FIG. 5, a pedestal 131 may be located between the electrode 130 and an external surface of the balloon 120 to increase a height of the electrode 130 above said external surface. Without pedestal 131, the height of the electrode 130 per se may be for example 0.05 mm as measured from the balloon surface. With pedestal 131, the height of the electrode 130 may be for example 0.05 mm~2 mm (preferably 0.05 mm~2 mm) as measured from the balloon surface. The pedestal 131 may be a pressure sensor, or a simple conductor. The shape of electrode 130 may be designed as a blade for cutting into and anchoring to a tissue. To reinforce the anchoring, the blade may have one or more hooks. A pressure sensor may be useful to monitor and control the pressure that is applied to for example the stenosis, when the surface of inflated balloon 120 is compressing the lesion, pushing it radially outward and widening or restoring the luminal diameter of the vessel.

In various embodiments of the invention, stent 110 may be excluded from medical device 100. As a result, device 100 may include a balloon 120, an electrode 130, and a pedestal 131 such as a pressure sensor. Similarly, pedestal 131 is located between the electrode 130 and an external surface of the balloon 120 to increase a height of the electrode 130 above said external surface. In a preferred embodiment, electrode 130 is a blade for cutting into and anchoring to a tissue, and the blade has one or more hooks to reinforce the anchoring to the tissue.

Figure 6:
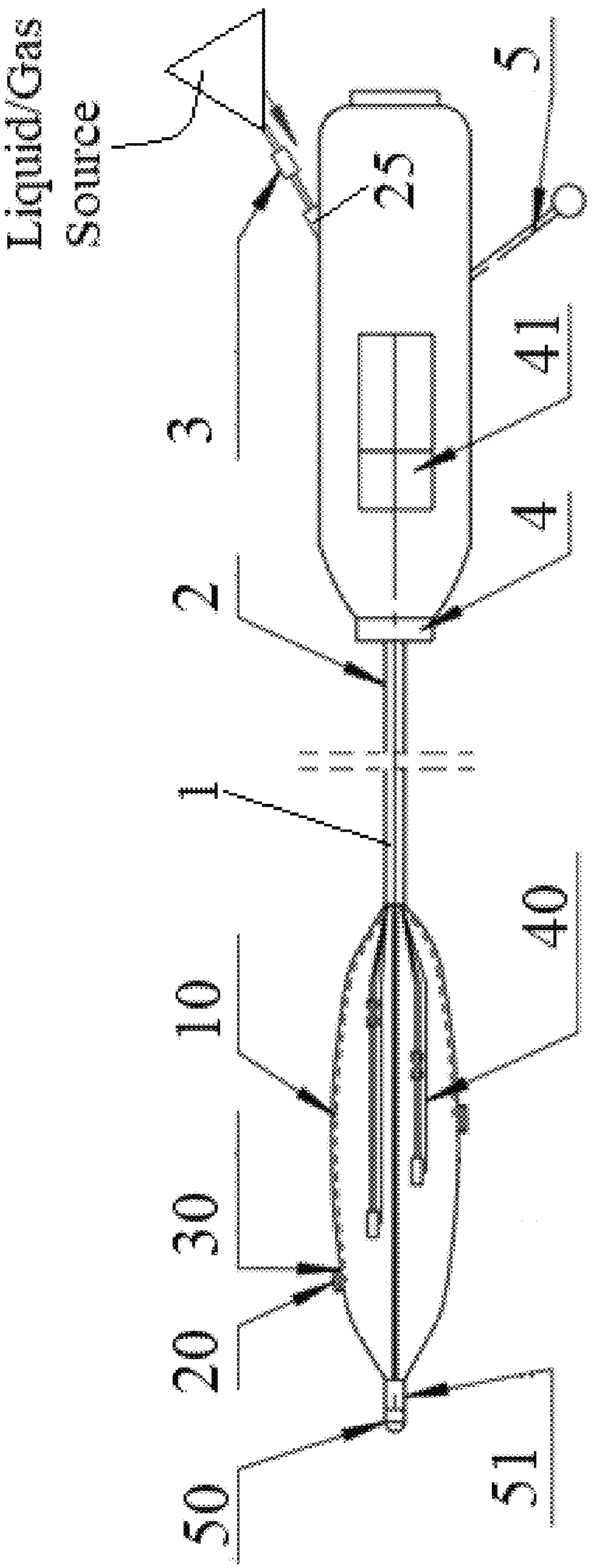
FIG. 6 schematically shows a balloon catheter in accordance with an exemplary embodiment of the present invention.

An example of the medical device according to the present invention is any known balloon catheter, for inserting into a tissue lumen or a channel within a tubular tissue structure, such as a blood vessel (including an artery or a vein), a cavity within a hollow portion of an organ, such as an intestine, an oral canal, a heart, a kidney, or auditory canal. FIG. 6 shows a balloon catheter for radiofrequency ablation, and well-known components in such a balloon catheter are shown in simplified form, omitted, or merely suggested, in order to avoid unnecessarily obscuring the present invention. With reference to the plan view of FIG. 6, the balloon and electrode assembly is configured at the distal end of the catheter 1. Catheter 1 includes a handle 4, a flexible long tube or shaft 2 extending distally from handle 4 to an expandable and inflatable balloon 10 and terminating at catheter distal tip, which may be a front image sensor 50 secured with a distal end connector 51. As known in the art, tube or shaft 2 may include a lumen, one or more layers coaxially surrounding the lumen, and electrically conducting wire(s) wedged between layers for delivering RF energy. Electrically conductive wire may be made of material such as nitinol or copper. Depending on use, the catheter may have a single lumen (a “monoluminal catheter”) or multiple lumens. A catheter with two lumens is “biluminal”, three “triluminal”. Up to 4 or 5 lumens may be used, allowing multiple drugs and devices to be delivered and monitored simultaneously. Therefore, tube or shaft 2 may include one or more lumens for e.g. insertion of a guidewire to assist in advancing the catheter to the target site. At least one of the lumens is configured to receive inflation media and pass such media to balloon 10 for its expansion.

Handle 4 may connect to one or more suitable accessary devices, such as a source of inflation media (e.g., air, saline, or contrast media). Handle 4 may include a port opening 25 in communication with tube 2 for the injection and aspiration of fluid (from a liquid/gas source a shown) to inflate and deflate the balloon 10 during use under the control of pressure control 3. Balloon 10 may be coaxially arranged around tube 2 near the distal end and is shown in an expanded state. The balloon catheter 1 may be a rapid exchange or over-the-wire catheter and made of any suitable biocompatible material. For example, handle 4 may include a side-arm extension on with an opening to allow the insertion of a guidewire to facilitate tracking through the vessel. Pull wire 5 (e.g. for controlling image sensor 50) and push/pull button 41 may be constructed with the handle 4. Electrode 20 and pressure sensor 30 may be placed on the surface of balloon 10 (either side-by-side or stacked as shown in FIG. 5), and thermal couple 40 is placed inside balloon 10 for measuring temperature. Thermal couple 40 is preferably placed near the RF electrode, either on the external or internal surface of the balloon.

Figure 7:
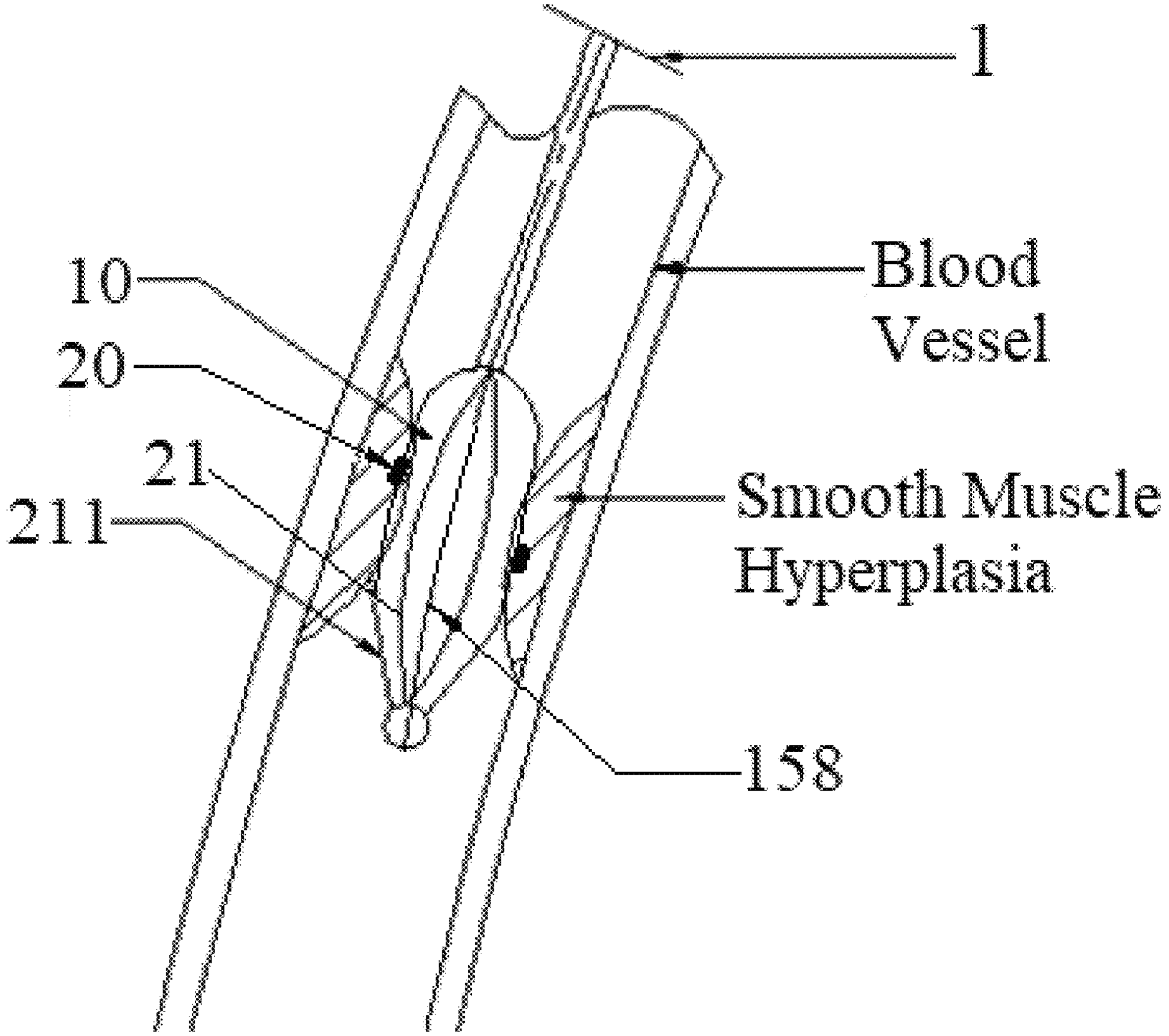
FIG. 7 is shows the balloon is expanded and inflated so as to contact smooth muscle hyperplasia in a blood vessel in accordance with an exemplary embodiment of the present invention.

With reference to FIG. 7, balloon 10 may be dressed or jacketed with a stent 21 consisting of stent wires 211 which can be maneuvered (e.g. expanded or shrunk) by adjusting wire 158. Stent 21 may be self-expandable. Alternatively, stent 21 may not be self-expandable (inactive), but it can be expanded by the expanding balloon 10. The balloon-stent assembly is placed in a vessel lumen which is narrowed due to hyperplasia (hypergenesis), neoplasia or benign tumor, and hypertrophy. Hyperplasia or hypergenesis is an increase in the amount of organic tissue that results from cell proliferation. Hyperplasia is a common preneoplastic response to stimulus, and the cells resemble normal cells but are increased in numbers, while the adaptive cell change in hypertrophy is an increase in the size of cells. Take smooth muscle hyperplasia as an example. Human arteries and veins are comprised of three layers: the intima which is the thinnest and innermost layer; the media which is the thickest and middle layer; and an outer adventitia layer comprised of connective tissue. The medial layer is comprised mainly of smooth muscle cells which play a prominent role in restenosis of previously treated vessels. In reaction to the vessel wall trauma associated with previous balloon angioplasty, the smooth muscle cells within the medial layer proliferate causing a thickening of the overall vessel wall and consequently, a reduction in the luminal diameter of the vessel.

Figure 8:
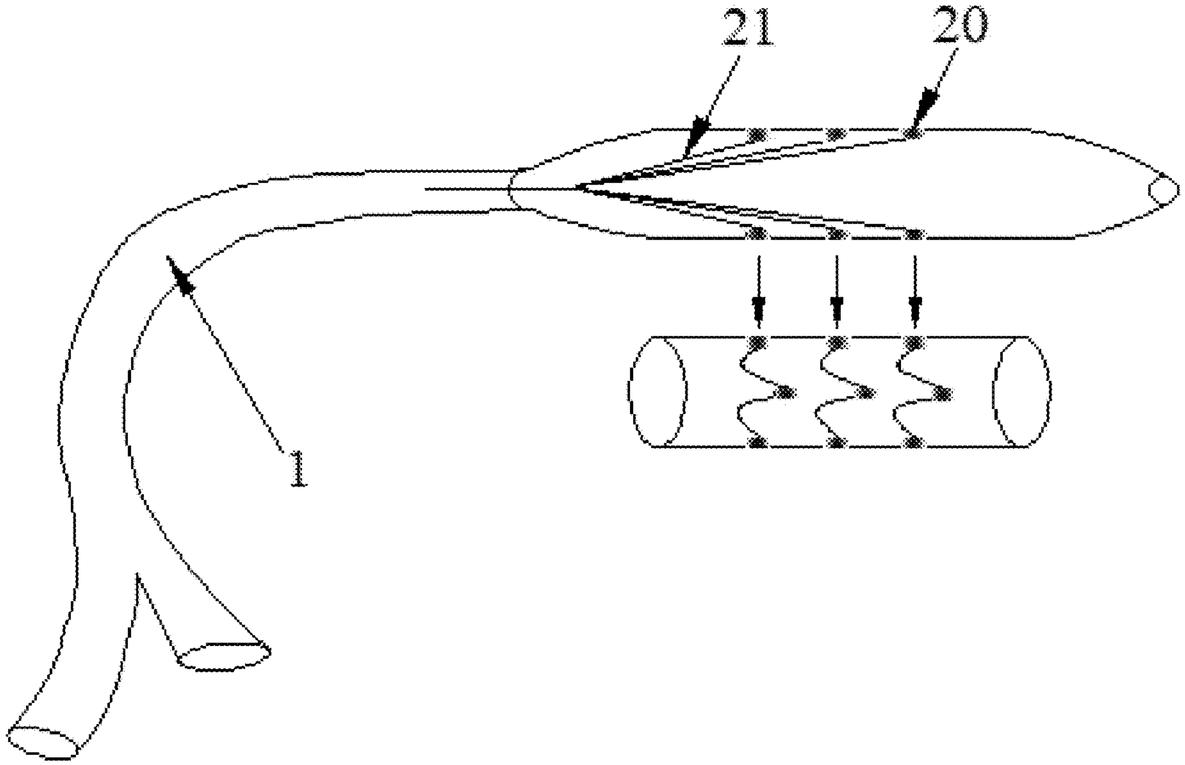
FIG. 8 illustrates a configuration wherein the stent has never been linked to the balloon in accordance with an exemplary embodiment of the present invention.

Stent 21 may be a basket-type stent and expandable and shrinkable, and may be attached to balloon 10. Alternatively, stent 21 may be detachable or separable from balloon 10. As shown in FIG. 8, stent 21 may be attached to balloon 10 or detached from balloon 10.

Figure 9A:
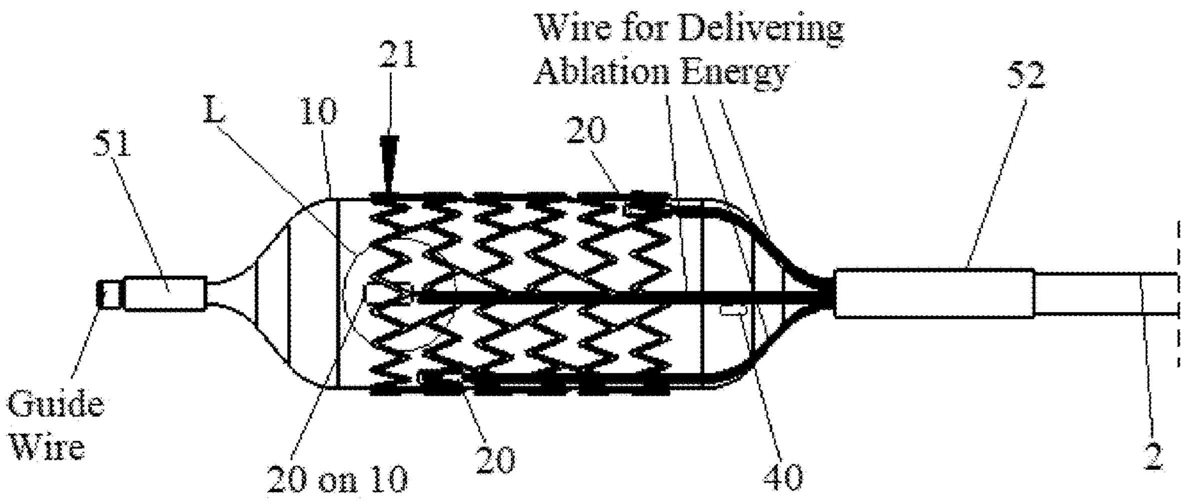
FIG. 9A demonstrates a specific stent-balloon assembly structure in accordance with an exemplary embodiment of the present invention.
Figure 9B:
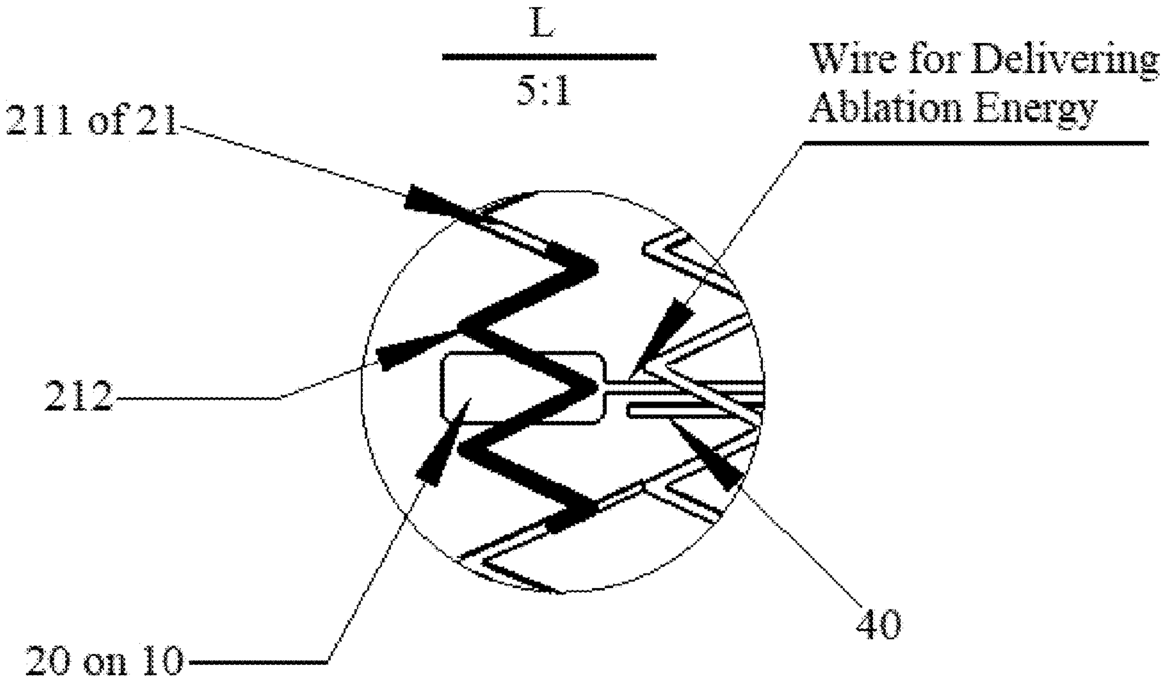
FIG. 9B depicts stent wires being used as electrode extender in accordance with an exemplary embodiment of the present invention.

With reference to FIG. 9A, a few electrodes 20 are adhered to surface of balloon 10, and wires for delivering ablation energy to electrodes are bundled into proximal end connector 52. Stent 21 contacts at least some of electrodes 20. As shown in the enlarged view of FIG. 9B, a portion of stent wire 211 becomes electrode extender 212 for ablating nearby tissue, and they work together like 130 and 111 as shown in in FIG. 3.

Figure 12:
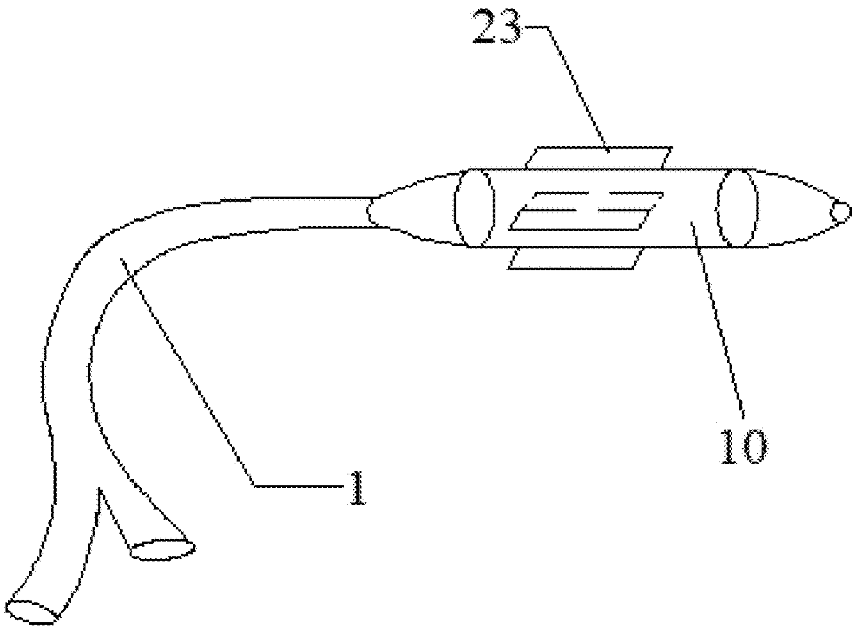
FIG. 12 shows a specific design of an electrode on balloon skin with or without a stent in accordance with an exemplary embodiment of the present invention.
Figure 13:
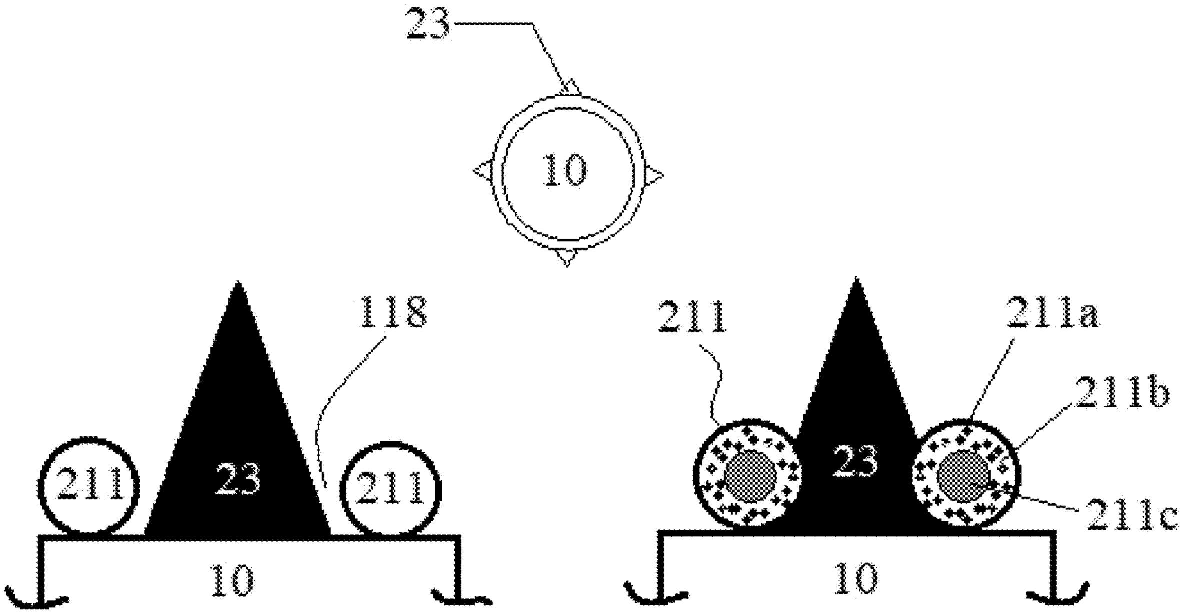
FIG. 13 illustrates an electrode blade and its interaction with a stent wall in accordance with an exemplary embodiment of the present invention.

The medical device of the invention may be a stented or non-stented balloon catheter. As shown in FIG. 12 and FIG. 13, electrodes 20 (with stent 21 or without stent 21) may be built like cutting blades 23. In an embodiment, cutting blades 23 may be tapered, with a sharp tip distal from the balloon 10 and a large base proximal to the balloon 10. The base of electrode blade 23 may have a shape (e.g. triangle) conforming to the shape of the radial opening 118 (e.g. triangle). When the base of 23 is smaller than the radial opening 118 and when the balloon 10 is inflated, the entire electrode blade 23 can protrude through radial opening 118 without contacting/cutting stent wire 211. When the base of 23 is bigger than the radial opening 118 and when the balloon 10 is inflated, the electrode blade 23 will be stuck by radial opening 118 at its base, and 1, 2, 3 or 4 blades of electrode 23 may be forced to cut into stent wire 211. This is particular useful for stent wire 211 with a chemically inert sealing skin 211*a*, a metal core 211*c*, and a drug releasing shell 211*b* between 211*a* and 211*b*. Blades of electrode 23 may cut skin 211*a*, and make one or more openings on skin 211*a*. Drug releasing shell 211*b* can then start to release pharmaceuticals through the one or more openings on skin 211*a*. These pharmaceuticals can be any known drugs used in drug-eluting stents (DES), for example, to suppress growth of scar tissue along the inner vessel wall over an extended period of time. For example, anti-restenosis drug may be selected from the group consisting of paclitaxel and vasculant. The drug is slowly released or eluted, thus fighting fibrosis and reducing the occurrence and extent of re-stenosis when compared with bare stents. As compared to traditional "drug-eluting stents (DES)" that are coated in medication without skin 211*a*, the drug releasing from the DES of the invention as shown in FIG. 13 is even slower, due to a limited number exiting openings on skin 211*a*.

Figure 14:
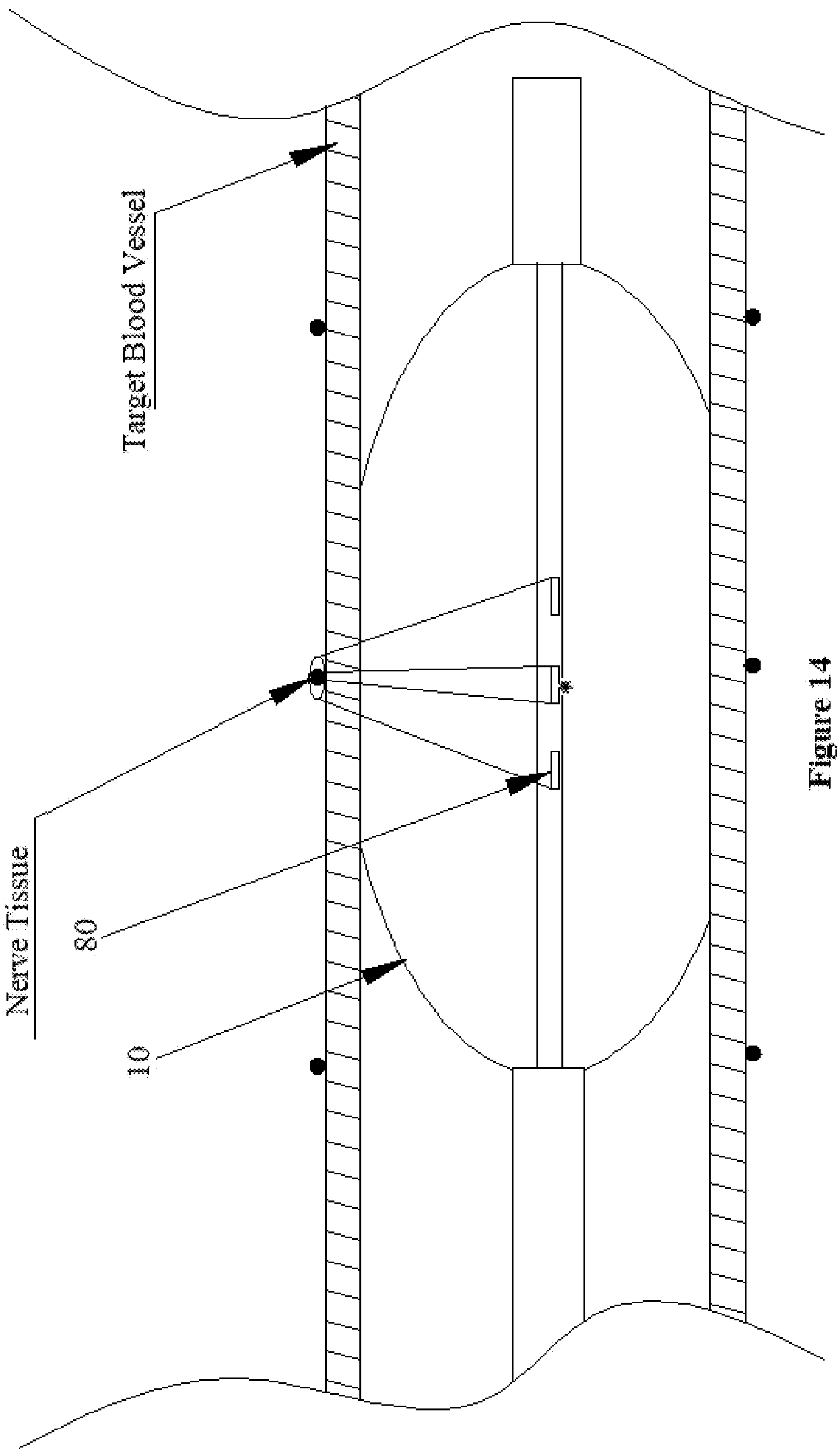
FIG. 14 demonstrates a balloon catheter with an ultrasonic wave generator for denervation in accordance with an exemplary embodiment of the present invention.
Figure 15:
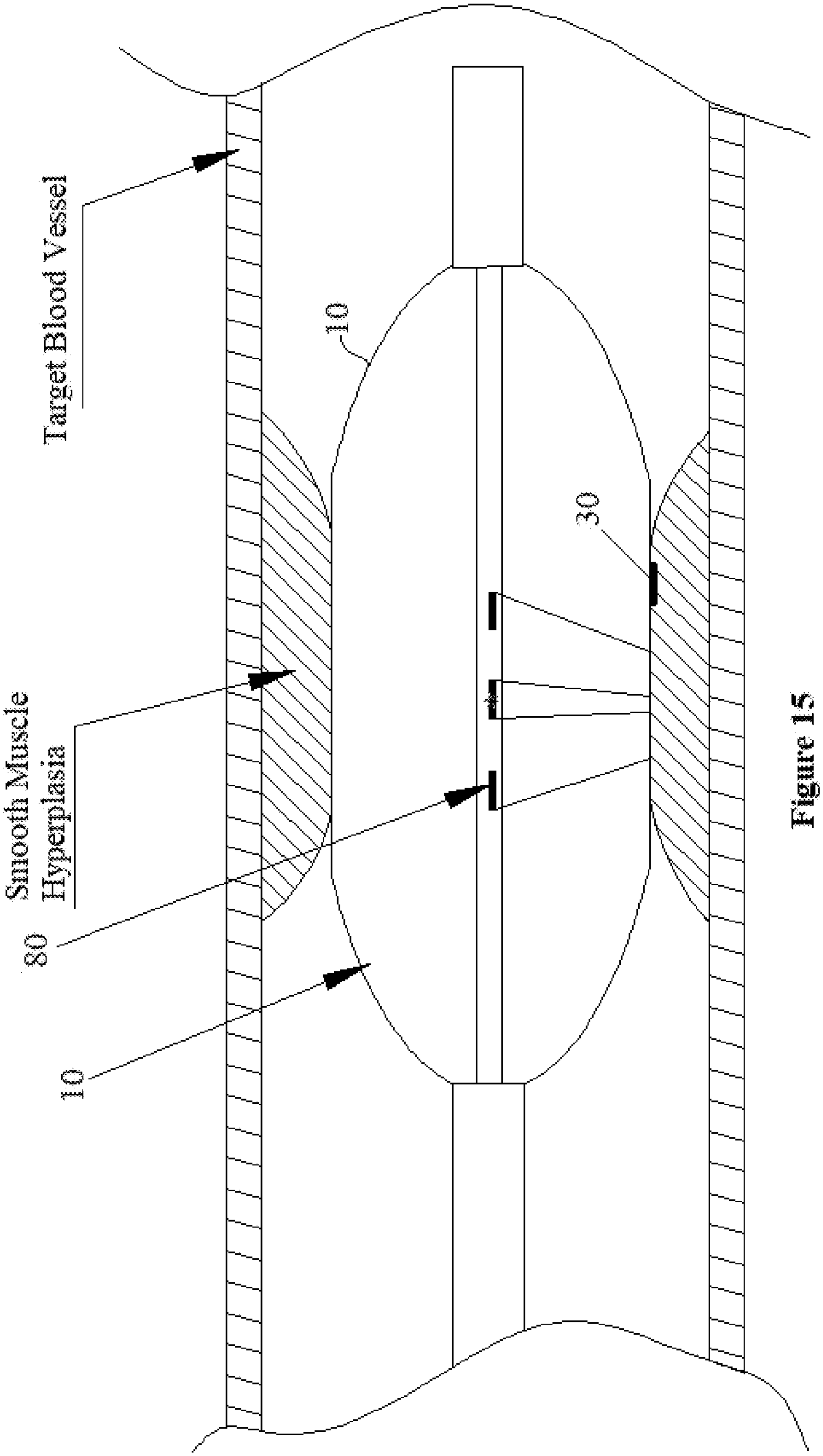
FIG. 15 depicts a balloon catheter with an ultrasonic wave generator for ablating smooth muscle hyperplasia in accordance with an exemplary embodiment of the present invention.

It should be appreciated that ablation member 139 may be an ultrasonic wave generator 80 within balloon 10, as shown in FIG. 14. Energy from ultrasonic wave generator 80 may be employed to accomplish denervation of the nerve tissues on a target blood vessel. Energy from ultrasonic wave generator 80 may also be employed to accomplish ablation of smooth muscle hyperplasia in a blood vessel, as shown in FIG. 15.

Figure 16:
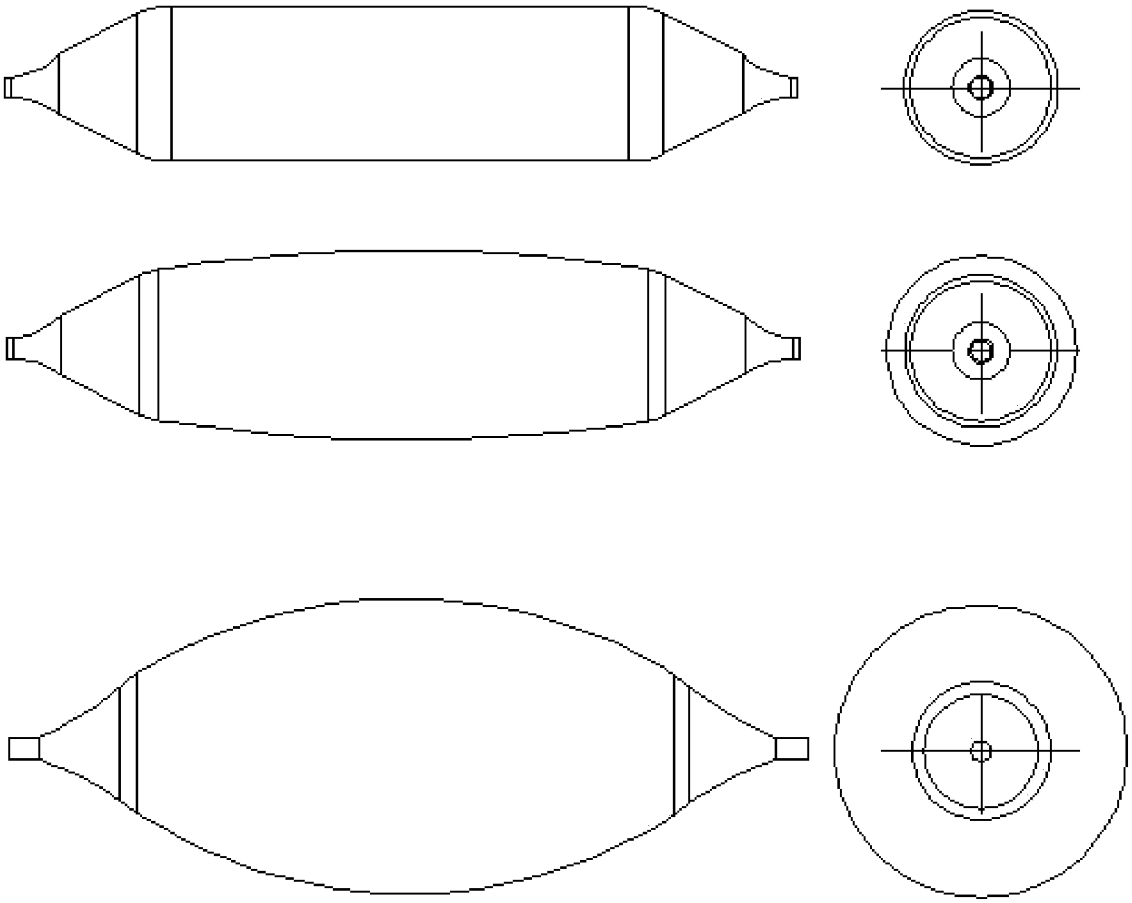
FIG. 16 schematically shows balloons of different shapes in the medical device in accordance with an exemplary embodiment of the present invention.
Figure 17:
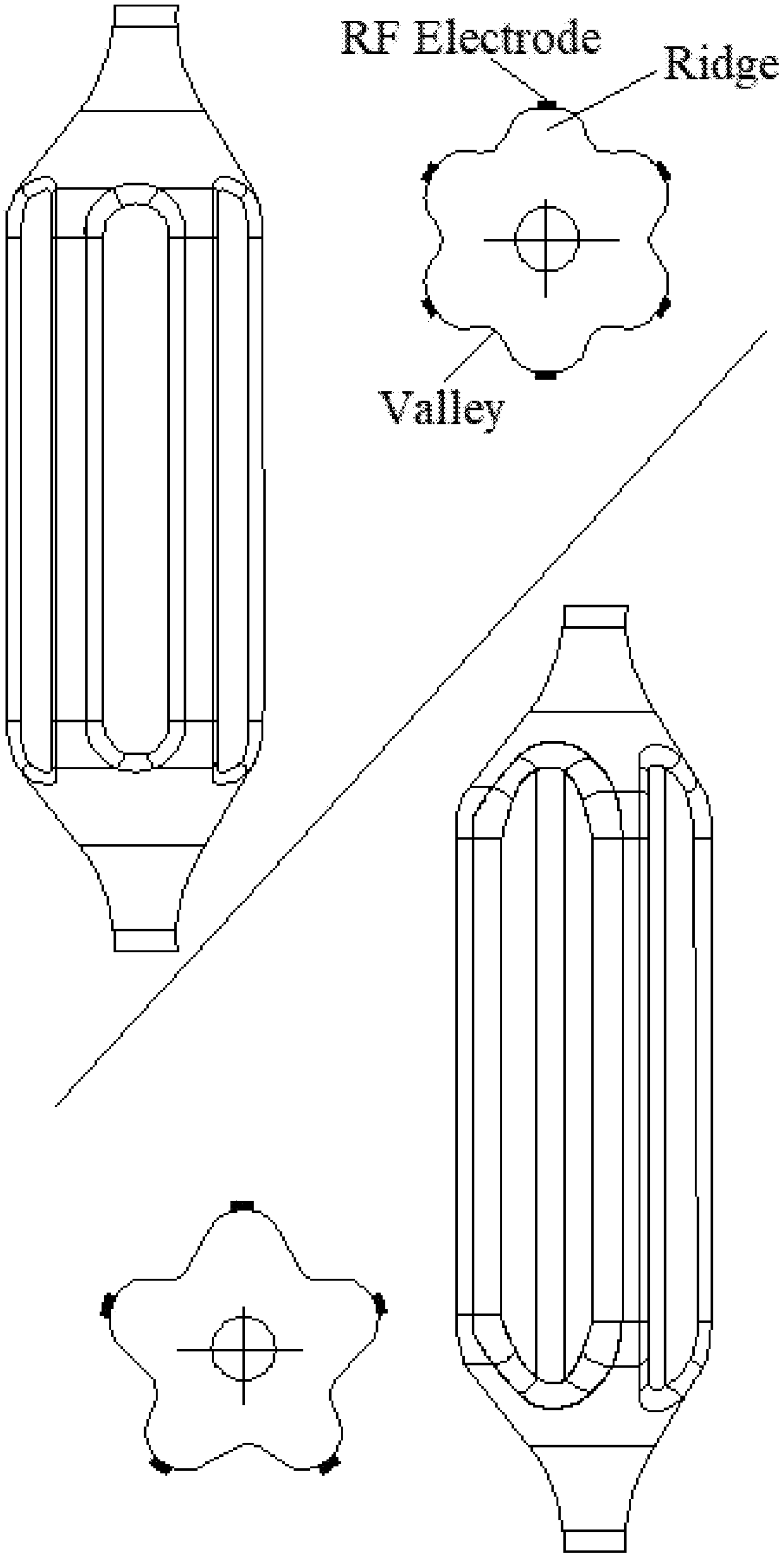
FIG. 17 demonstrates some balloon designs with ridges for placing RF electrodes on their tips in accordance with an exemplary embodiment of the present invention.
Figure 18:
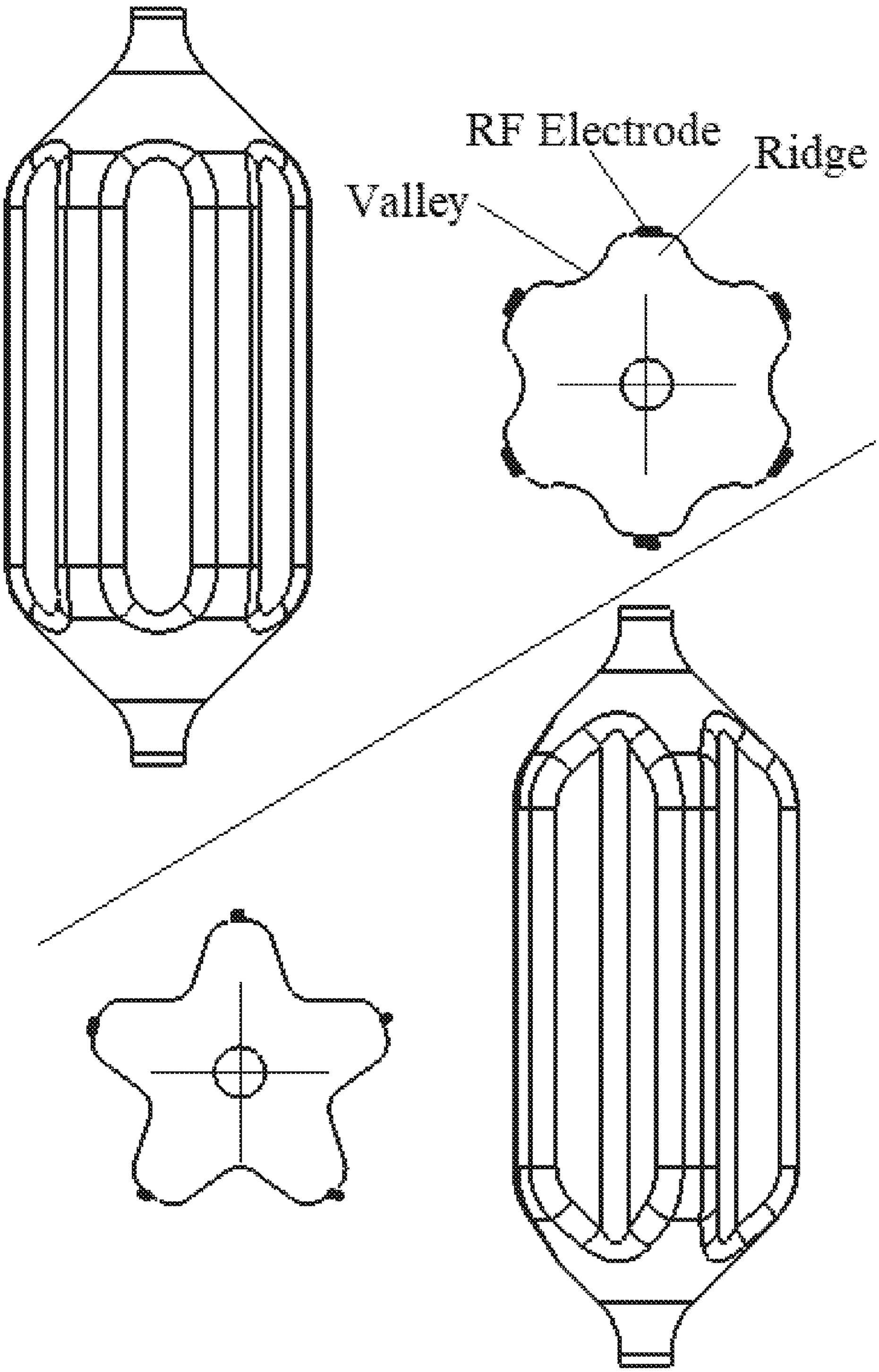
FIG. 18 depicts other balloon designs with ridges for placing RF electrodes on their tips in accordance with an exemplary embodiment of the present invention.

FIGS. 16-18 show various shapes of balloon 10/120. Fold balloons have folds in the compressed state of the balloon that open at least partially when expanding the balloon. For example, the inflatable body of balloon 10/120 can have a cylindrical morphology, a cone shaped morphology or dog-bone shaped morphology, an "onion"-shaped morphology, or a barrel-like morphology. In another embodiment, the inflatable body may have a compound shape. For example, the inflatable body may be rounded in shape in certain portions, and include at least one portion that is flattened. In another example, the inflatable body may be configured as a flattened stretchable portion that can be expanded or collapsed. In an implementation, such a flattened portion of the inflatable body may be deployed to make substantially full contact with a portion of a tissue, e.g., as part of a tissue lumen.

As show in FIGS. 17-18, balloon 10/120 in expanded state may have a few ridges and a few valleys, and electrode 20/130 may be placed on tips of the ridges.

The medical process of the invention may first involve diagnosing a human subject suffering from disease such as coronary artery disease and specifically identifying a target area of an artery in the subject which is partially blocked by plaque. A procedure is then planned whereby blockage in the target area is moved or removed from the artery so as to increase blood flow through the target area of the artery.

Various embodiments of the invention provide a medical process comprising these steps: providing a medical device 100 comprising a balloon 120 and an electrode 130 (as described above); maneuvering the balloon 120 and the electrode 130 near a target tissue; inflating or deflating the balloon 120 so that the electrode 130 contacts the tissue with a controllable contacting pressure; and ablating the tissue only when the contacting pressure falls within a predetermined range. In an example, inflating and ablating are carried out simultaneously, particularly when the contacting pressure is set as a specific value (not a range), in which situation the ongoing ablation keeps decreasing the contacting pressure, which in turn triggers continuous inflating of the balloon to meet the pressure requirement.

The method may be used in, for example, a central venous catheter (CVC) procedure. CVS can be placed in veins in the neck (internal jugular vein), chest (subclavian vein or axillary vein), groin (femoral vein), or through veins in the arms. Before insertion, the patient is first assessed by reviewing relevant labs and indication for CVC placement, in order to minimize risks and complications of the procedure. Next, the area of skin over the planned insertion site is cleaned. A local anesthetic is applied if necessary. The location of the vein is identified by landmarks or with the use of a small ultrasound device. A hollow needle is advanced through the skin until blood is aspirated. The color of the blood and the rate of its flow help distinguish it from arterial blood (suggesting that an artery has been accidentally punctured). A blunt guide wire is passed through the needle, and then the needle is removed. A dilating device may be passed over the guide wire to expand the tract. Finally, the central line itself is then passed over the guide wire, which is then removed. All the lumens of the line are aspirated (to ensure that they are all positioned inside the vein) and flushed with either saline or heparin. Electromagnetic tracking can be used to verify tip placement and provide guidance during insertion. The catheter is held in place by an adhesive dressing, suture, or staple which is covered by an occlusive dressing. Regular flushing with saline or a heparin-containing solution keeps the line open and prevents blood clots. Certain lines are impregnated with antibiotics, silver-containing substances (specifically silver sulfadiazine) and/or chlorhexidine to reduce infection risk.

The method may be used in, for example, percutaneous transluminal angioplasty (PTCA). Such minimally invasive procedure is designed to open blocked coronary arteries, allowing blood to circulate unobstructed to the heart muscle. The procedure begins with the injection of local anesthesia into the groin area and putting a needle into the femoral artery. A guide wire is placed through the needle and the needle is removed. An introducer is then placed over the guide wire, after which the wire is removed. A different sized guide wire is then put in its place. Next, a long narrow tube called a diagnostic catheter is advanced through the introducer over the guide wire, into the blood vessel. This catheter is then guided to the aorta and the guide wire is removed. Once the catheter is placed in the opening (or ostium) of one the coronary arteries, a contrast dye may be injected and an x-ray may be taken. If a treatable blockage is noted, the first catheter is exchanged for a guiding catheter. Once the guiding catheter is in place, a guide wire is advanced across the blockage, and then the balloon catheter is advanced to the blockage site. The balloon is inflated for a few seconds to compress the blockage against the artery wall.

The method may also be used in, for example, RFA or rhizotomy to treat severe chronic pain in e.g. the lower (lumbar) back, as shown in FIG. 14. Radio frequency waves are used to produce heat on specifically identified nerves surrounding the facet joints on either side of the lumbar spine. By generating heat around the nerve, the nerve gets ablated thus destroying its ability to transmit signals to the brain. The nerves to be ablated are identified through injections of local anesthesia (such as lidocaine) prior to the RFA procedure. If the local anesthesia injections provide temporary pain relief, then RFA is performed on the nerve(s) that responded well to the injections.

In some embodiments, the medical process of the invention includes steps of: providing a medical device 100 with a balloon-stent assembly 101 comprising a stent 110, a balloon 120 within the stent 110, and an electrode 130 (as described above); maneuvering the balloon-stent assembly 101 near a target tissue in a first location with a first orientation; inflating or deflating the balloon 120 so that the electrode 130 contacts the tissue with a controllable contacting pressure; ablating the tissue only when the contacting pressure falls within a predetermined range; withdrawing the balloon 120 from inside the stent 110 and leaving the stent 110 in said first location (or rotating the balloon 120 to a second orientation at the first location); maneuvering the balloon 120 to a tissue in a second location; and ablating the tissue in said second location. In an example, inflating and ablating are carried out simultaneously, particularly when the contacting pressure is set as a specific value (not a range), in which situation the ongoing ablation keeps decreasing the contacting pressure, which in turn triggers continuous inflating of the balloon to meet the pressure requirement. When tether 140 is present, the method will further include a step of breaking the tether when withdrawing the balloon 120 from inside the stent 110.

Figure 10:
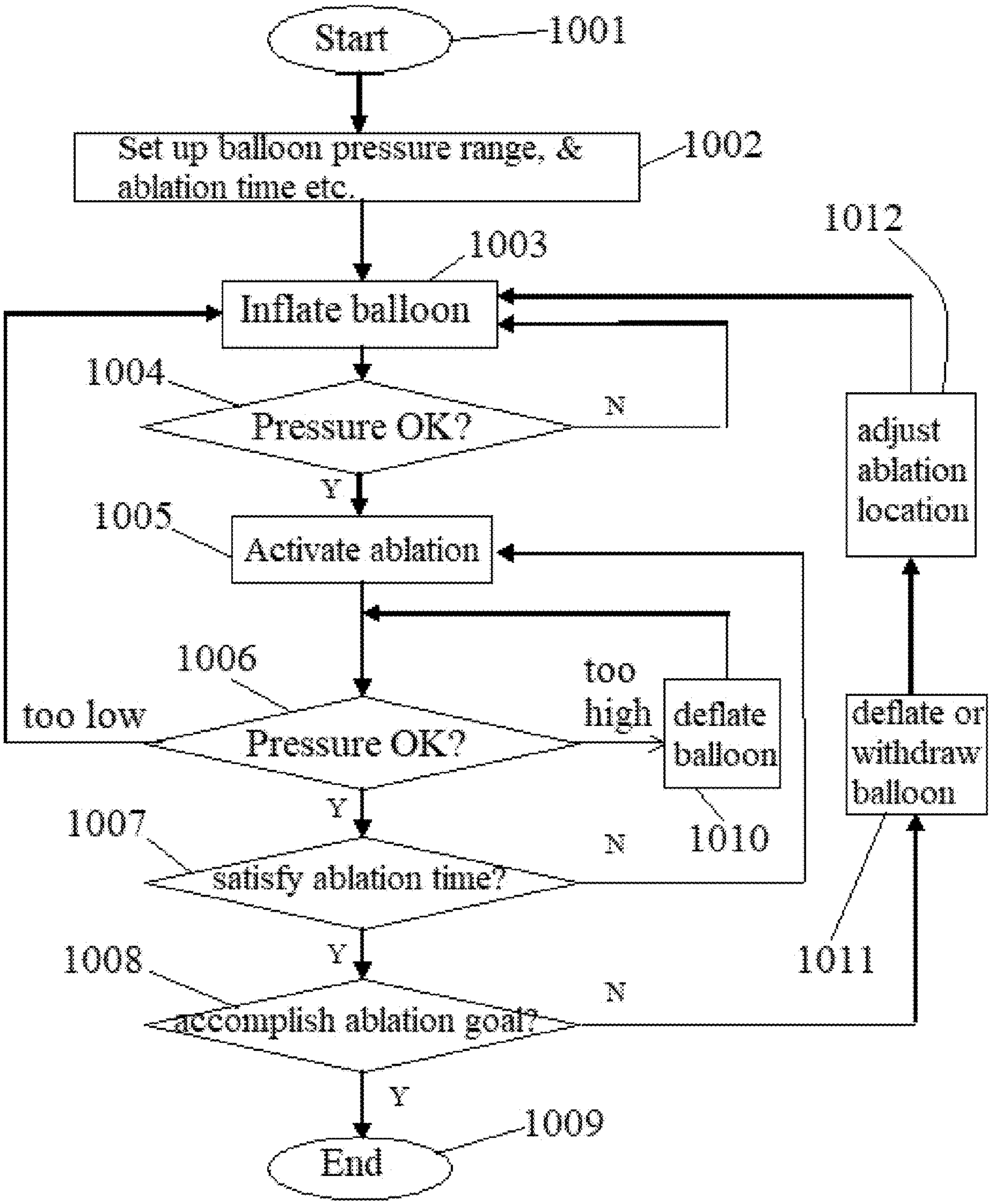
FIG. 10 is a flow chart of an exemplary medical process in accordance with an exemplary embodiment of the present invention.

With reference to the flow chart of FIG. 10, a specific medical process using the medical device as described above and characterized by "constant balloon pressure" may include the following steps: at 1001—start; at 1002—set up balloon pressure range (e.g. 3-30 atmospheres (ATM), 5-7 ATM such as 6 ATM, or 4-6 ATM), temperature, impedance, resistance, power, and ablation time etc. The RFA is typically carried out using a voltage and a current with defined ranges over a defined period of time. At 1003—inflate the balloon after it is inserted to and placed at a desired location. At 1004—check if the balloon pressure is within the range; if yes, then goes to 1005 to activate the ablation process; if no, then go back to 1003 and continue to inflate the balloon.

After 1005, recheck at 1006 if the balloon pressure is still within the range; if the balloon pressure at 1006 is higher than the range, then goes to 1010 to deflate the balloon and then proceed to 1006 again to recheck if the balloon pressure falls down into the range; if the balloon pressure at 1006 is within the range, then move to 1007 to determine if ablation time is satisfied; if not, then go back to 1005 and continue the ablation; if yes, then move forward to 1008 to determine if the ablation goal has been accomplished (e.g. by examining real-time X-ray imaging); if not, then move to 1011 and deflate (and/or withdraw) the balloon, and then at 1012 adjust the ablation to a new site/location or a new orientation at the same location. At the new site/location or new orientation, the process starts from 1003. If at 1008 the ablation goal has been accomplished, the medical process is then ended at 1009.

Figure 11:
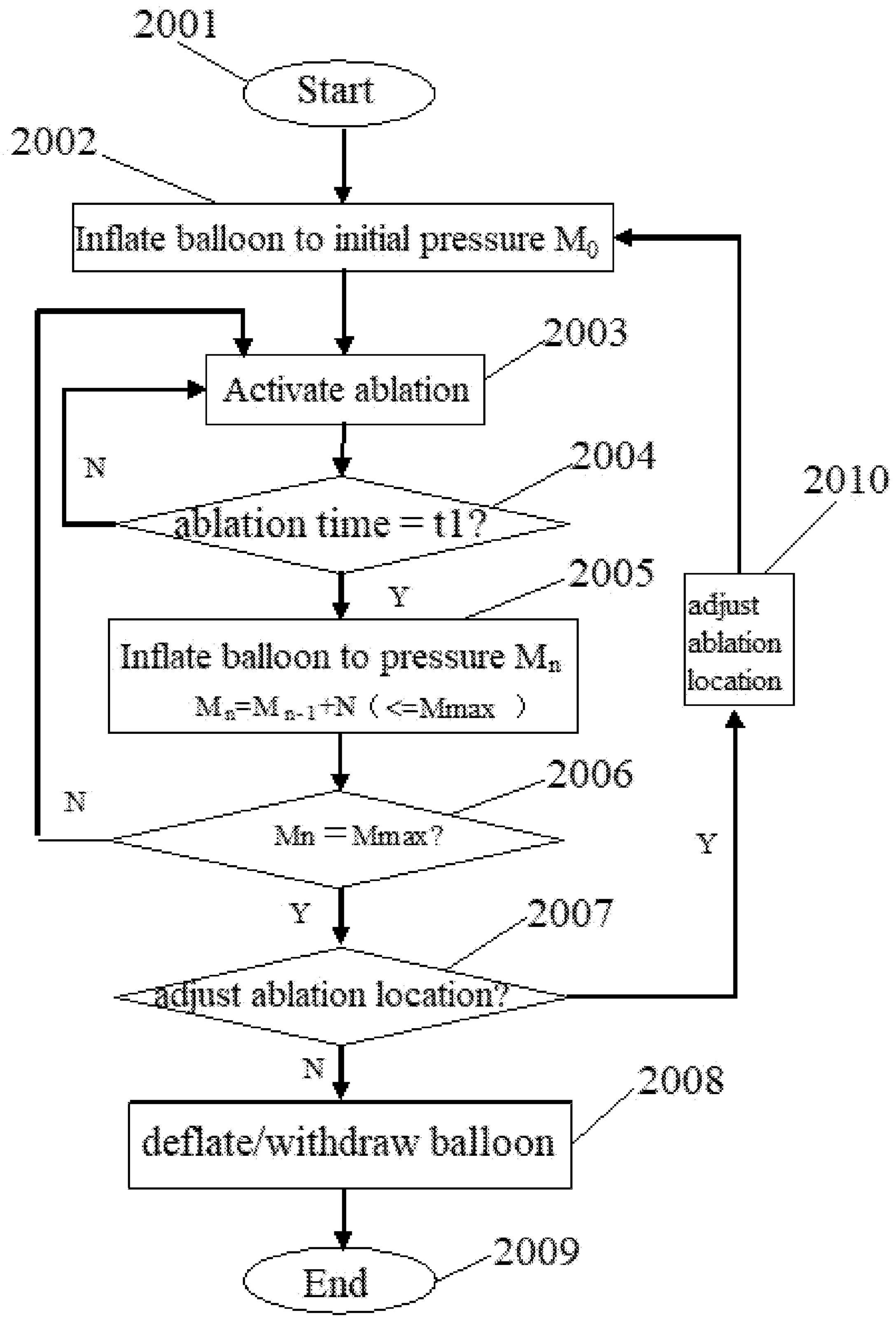
FIG. 11 is another flow chart of an exemplary medical process in accordance with an exemplary embodiment of the present invention.

With reference to the flow chart of FIG. 11, another specific medical process using the medical device as described above and characterized by "variable balloon pressure" or "increasing balloon pressure" may include the following steps: at 2001—start; at 2002—inflate the balloon to an initial pressure M0 after it is inserted to and placed at a desired location; at 2003—activate the ablation process; determine at 2004 if ablation time t1 is satisfied; if t1 is not satisfied, then move back to 2003 and continue the ablation; if t1 is satisfied, then move to 2005 and inflate the balloon to pressure $M_n$, wherein $M=M_{n-1}+N$, N is the incremental increase of the balloon pressure and $M_n$ should not be higher than a predetermined pressure threshold $M_{max}$ for safety. N may be a constant value; or N may be decreasing as corresponding n is increasing. At 2006, determine if $M_n=M_{max}$. If $M_n$ remains lower than $M_{max}$, then move back to 2003 and continue the ablation; if $M_n$ reaches $M_{max}$, then determine whether the process needs to adjust the ablation to a new site/location or a new orientation at the same location. If it needs, then go to 2010 to adjust the ablation to a new site/location or new orientation, and start over from 2002. If it does not need, then at 2008 deflate the balloon and withdraw it from the site, and the medical process is then ended at 2009.

For multiple electrodes 20, they may experience different contacting pressures. In this situation, each electrode may be individually controlled by the system to release RF energy when it is ready.

An advantage of the invention is that, with a single catheter of the invention, the doctor can treat vessels or vessel segments with a big range of diameters, for example from 4 mm to 12 mm, avoiding frequent change of catheters of different sizes.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, processor-executed, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or executable instructions that, when executed by one or more processor devices, cause the host computing system to perform the various tasks. In certain embodiments, the program or code segments are stored in a tangible processor-readable medium, which may include any medium that can store or transfer information. Examples of suitable forms of non-transitory and processor-readable media include an electronic circuit, a semiconductor memory device, a ROM, a flash memory, an erasable ROM (EROM), a floppy diskette, a CD-ROM, an optical disk, a hard disk, or the like.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A medical device with a balloon-stent assembly comprising a balloon expandable stent, a balloon within the balloon expandable stent, and a breakable tether that links the balloon expandable stent and the balloon;

wherein the breakable tether does not wrap around the stent and is not a restraining tether that restrains an expansion of the stent;

wherein the breakable tether does not wrap around the balloon; and wherein the breakable tether is so configured that, while the balloon expandable stent is being expanded by the balloon and after the balloon expandable stent has been expanded by the balloon and has been placed in a position in a tissue lumen or a channel within a tubular tissue structure, the breakable tether does not break apart; but while the balloon is being moved away from the already-placed balloon expandable stent or after the balloon is moved away from the already-placed balloon expandable stent, the breakable tether breaks apart without disrupting the position of the already-placed balloon expandable stent.

2. The medical device according to claim 1, wherein the breakable tether does not go between any two wires of the stent.

3. The medical device according to claim 1, wherein the breakable tether is entirely placed within a space between the balloon expandable stent and the balloon before it breaks apart; and wherein the breakable tether does not wrap around the balloon before or after it breaks apart.

4. The medical device according to claim 1, wherein the breakable tether includes a snap fastener as a breakable point, and wherein the tissue lumen or the channel within a tubular tissue structure is a blood vessel, or a cavity within a hollow portion of an organ, an oral canal, a heart, a kidney, or auditory canal.

5. The medical device according to claim 1, wherein the breakable tether includes a breakable point.

6. The medical device according to claim 1, wherein the breakable tether includes a breakable point, and wherein a length from the breakable point to the balloon expandable stent along the breakable tether is less than 30% of a total length of the breakable tether.

7. The medical device according to claim 1, further comprising an ablation member.

8. The medical device according to claim 7, wherein the ablation member is an electrode on an external surface of the balloon;

wherein the electrode is a blade for cutting into, and anchoring to, a tissue;

wherein the balloon expandable stent includes a radial opening, and the electrode extends beyond the balloon expandable stent, or protrudes out from the balloon expandable stent, through the radial opening to contact a tissue outside the balloon expandable stent;

wherein the radial opening is defined by a net wire; and wherein the electrode is directly placed on the external surface of the balloon or wherein a conductor pedestal is located between the electrode and the external surface of the balloon.

9. The medical device according to claim 7, wherein the ablation member is an electrode on an external surface of the balloon.

10. The medical device according to claim 9, further comprising a pedestal located between the electrode and the external surface of the balloon to increase a height of the electrode above said external surface.

11. The medical device according to claim 10, wherein the pedestal is a pressure sensor.

12. The medical device according to claim 9, wherein the electrode is a blade for cutting into and anchoring to a tissue.

13. The medical device according to claim 12, wherein the blade comprises a hook to reinforce said anchoring to the tissue.

14. The medical device according to claim 7, wherein the stent includes an electrode extender that functions as the ablation member; an electrode contacts the electrode extender from inside the stent; and the electrode electrically communicates to a tissue outside the stent through the electrode extender.

15. The medical device according to claim 14, wherein the electrode extender is a blade for cutting into and anchoring to the tissue.

16. The medical device according to claim 15, wherein the blade comprises a hook to reinforce said anchoring to the tissue.

17. The medical device according to claim 7, wherein the stent includes a radial opening, and an electrode extends beyond the stent, or protrudes out from the stent, through the radial opening to contact a tissue outside the stent.

18. The medical device according to claim 17, wherein the radial opening is defined by a net wire.

19. The medical device according to claim 7, wherein the ablation member is an ultrasonic wave generator inside the balloon or an electrode on an external surface of the stent.

* * * * *